United States Patent
Burbank et al.

[11] Patent Number: 5,931,801
[45] Date of Patent: Aug. 3, 1999

[54] VALVE PORT ASSEMBLY WITH INTERLOCK

[75] Inventors: Jeffrey H. Burbank, Boxford; James M. Brugger, Newburyport, both of Mass.

[73] Assignee: Vasca, Inc., Tewksbury, Mass.

[21] Appl. No.: 08/857,386

[22] Filed: May 15, 1997

[51] Int. Cl.[6] .................................. A61M 37/00
[52] U.S. Cl. ........................................... 604/4
[58] Field of Search .................. 604/8–10, 93, 604/86–88, 173–175, 244, 283

[56] References Cited

U.S. PATENT DOCUMENTS

| | | | |
|---|---|---|---|
| 4,108,173 | 8/1978 | Slivenko et al. | 128/214 |
| 4,673,394 | 6/1987 | Fenton, Jr. et al. | 604/175 |
| 4,692,146 | 9/1987 | Hilger | 604/93 |
| 4,695,273 | 9/1987 | Brown | 604/173 |
| 4,778,452 | 10/1988 | Moden et al. | 604/93 |
| 4,915,690 | 4/1990 | Cone et al. | 604/93 |
| 4,929,236 | 5/1990 | Sampson | 604/175 |
| 5,167,638 | 12/1992 | Felix et al. | 604/175 |
| 5,281,199 | 1/1994 | Ensminger et al. | 604/93 |
| 5,318,545 | 6/1994 | Tucker | 604/244 |
| 5,352,204 | 10/1994 | Ensminger | 604/93 |
| 5,356,381 | 10/1994 | Ensminger et al. | 604/93 |
| 5,360,407 | 11/1994 | Leonard | 604/175 |
| 5,395,324 | 3/1995 | Hinrichs et al. | 604/86 |
| 5,399,168 | 3/1995 | Wadsworth, Jr. et al. | 604/175 |
| 5,417,656 | 5/1995 | Ensminger et al. | 604/93 |
| 5,476,451 | 12/1995 | Ensminger et al. | 604/93 |
| 5,503,630 | 4/1996 | Ensminger et al. | 604/93 |
| 5,527,277 | 6/1996 | Ensminger et al. | 604/93 |
| 5,527,278 | 6/1996 | Ensminger et al. | 604/93 |

Primary Examiner—John G. Weiss
Assistant Examiner—Ki Yong O
Attorney, Agent, or Firm—Townsend Townsend & Crew LLP

[57] ABSTRACT

A dual port vascular access assembly comprises a first access port and a second access port. The linkage is coupled between the first access port to close the second access port in the absence of an access tube in the first access port. Such port assemblies are particularly useful for implantation in patients receiving hemodialysis. By connecting the first access port to the blood withdrawal side of the system, blood withdrawal will be automatically terminated upon cessation of blood returned to due loss of the return access tube in the port assembly.

28 Claims, 5 Drawing Sheets

5,931,801

VALVE PORT ASSEMBLY WITH INTERLOCK

BACKGROUND OF THE INVENTION

1. Field of the Invention

The present invention relates generally to the design and use of medical devices, and more particularly to the design and use of an implantable port assembly for establishing extracorporeal blood circulation for hemodialysis and other blood treatments.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for certain applications, such as intravenous feeding, intravenous drug delivery, and which are limited in duration, they are not suitable for hemodialysis and other extracorporeal procedures that must be repeated periodically, often for the lifetime of the patient.

For hemodialysis and other extracorporeal treatment regimens, a variety of implantable ports have been proposed over the years. Typically, the port includes a chamber and an access region, such as a septum, where the chamber is attached to an implanted catheter which in turn is secured to a blood vessel. In the case of veins, the catheter is typically indwelling and in the case of arteries, the catheter may be attached by conventional anastomosis.

Of particular interest to the present invention, needles and other access tubes may be percutaneously attached to an implanted port in several ways. Implantable ports often include a needle-penetrable septum which permits the percutaneous penetration of a needle into the internal chamber. The chamber, in turn, is connected to one end of the implanted catheter, and the other end of the catheter is indwelling in or otherwise attached to the blood vessel. Instead of a septum, the use of needle-actuated valve mechanisms in subcutaneously implanted ports has also been proposed. See, for example, U.S. Pat. No. 5,527,278, and copending provisional application Ser. No. 60/036,124, filed on Jan. 21, 1997 (attorney docket no. 17742-000600), the latter of which is assigned to the assignee of the present invention and is incorporated herein by reference. Both the septum ports and valve ports are most commonly provided in single-port assemblies, thus requiring two separate valve ports to establish access for blood extracorporeal circulation. The use of dual-port assemblies for establishing both blood access and blood return has also been proposed. See, for example, FIGS. 3 and 4 in U.S. Pat. No. 5,527,278.

A rare but serious risk in performing hemodialysis and other extracorporeal blood circulation procedures results from accidental disconnection of the blood return needle from the implanted blood return port. Because blood is usually returned to the patient on the low pressure, venous side of the vasculature, the extracorporeal circulation system (e.g., a dialysis machine) will not necessarily be able to detect any pressure change if a venous return needle is accidentally dislodged and lost from the patient's vein. The pressure sensed by the extracorporeal circulation system results primarily from the needle itself, so alarms built in to the circulation system are usually insufficient. Thus, since blood will continue to be drawn from the arterial side of the vasculature, the patient is at significant risk of losing large amounts of blood and even death.

For these reasons, it would be desirable to provide apparatus, systems, and methods which will reduce the risk of continued blood withdrawal during extracorporeal blood recirculation protocols in the event that the blood return needle or device becomes dislodged. In particular, it would be desirable to provide implantable port assemblies where the blood access or supply port is automatically closed in response to loss of the needle from the blood return port. Such assemblies could be in the form of dual port valve assemblies present in a single base or enclosure, or could be in the form of separately implantable single port valve assemblies where mechanical, fluid, or other coupling is provided for the interlock. The interlock provided will preferably be simple, reliable, and operate in a fail safe manner. Optionally, the port assemblies and methods may also provide for closure of the blood access port and the blood return ports on loss of the either the blood return needle or the blood access needle from the patient. At least some of the above objectives will be met by the different aspects of the present invention discussed below.

2. Description of the Background Art

Dual port vascular access assemblies are described in a number of U.S. Patents. U.S. Pat. Nos. 5,527,278; 5,527,277; 5,503,630; 5,476,451; 5,417,656; and 5,281,199, describe a dual port assembly suitable for performing hemodialysis. U.S. Pat. No. 4,108,173, describes dual port assemblies for withdrawing or introducing fluids from a single vessel. U.S. Pat. Nos. 5,399,168; 5,360,407; 5,167,638; and 4,692,146, describe dual port assemblies which are connected to blood vessels through a common lumen.

SUMMARY OF THE INVENTION

The present invention provides improved access port assemblies, apparatus, and methods which are useful for providing the simultaneous withdrawal and return of blood to a patient, usually while performing therapies requiring extracorporeal blood circulation, such as hemodialysis, hemofiltration, hemodiafiltration, apheresis, and the like. The apparatus and systems of the present invention will comprise a dual-port valve assembly or system including a first access port and a second access port. The first access port is connectable to a blood vessel or to a conduit which is connectable to a blood vessel. Similarly, the second access port is connectable to a blood vessel or to a conduit which is connectable to a blood vessel. The ports are accessible using needles or other access tubes which are percutaneously introduced and which establish a fluid connection with the blood vessel, optionally via the conduit. According to the present invention, a linkage or other interlock mechanism is provided which is coupled to the first access port and which closes the second access port in the absence of a needle or other access tube within the first access port. Thus, by relying on the first access port for blood return to the patient and the second access port for blood supply (to the extracorporeal circuit), the risk of continuing to draw blood from the second access port if the return tube is accidentally dislodged from the first access port is substantially reduced or eliminated.

In preferred aspects of the dual port valve assembly, the first linkage will also close the first access port when the return tube is absent from the first access port. In another preferred aspect, a second linkage may be provided which is coupled to the second access port and which closes both the first access port and the second access port in the absence of an access tube (in this case the blood withdrawal tube which supplies blood to the extracorporeal treatment system) in the second access port.

The dual port valve assembly will usually include all of its components within a single enclosure, referred to here and after as a "base." The components, however, may be separate in the form of a system with the first access port and second access port being separately implantable and connected by a mechanical or hydraulic linkage which is itself implanted between the two access ports. The nature of the linkage is not critical and can take virtually any form which senses the presence of an access tube within the access port and which is able to close either or both of the linked access ports whenever the access tube is removed therefrom. In a particularly preferred aspect, the linkage will be self-closing, i.e. insertion of a needle or other access tube will open the linked access port(s) against a spring or other force. When the access tube is removed, the port(s) will return to their normally closed configuration.

The first and second access ports will usually be connected to an artery as the blood supply source and a vein as the blood return, but other configurations are also possible. For example, the first and second access ports may be connected to a single blood vessel via a single, two-lumen conduit or via a pair of separate conduits. Alternatively, separate conduits may be used to connect to a vein as a blood supply source and an artery as a blood return source, although this will usually be the least preferred configuration.

In a specific embodiment of the present invention, the dual port valve assembly comprises a base having a venous passage for percutaneously receiving a venous access tube and an arterial passage for percutaneously receiving an arterial access tube. A venous conduit is disposed within the base to establish blood flow with the venous access tube which is inserted through the venous port. Similarly, an arterial conduit is disposed within the base to establish blood flow with the arterial access tube which is inserted through arterial port. A first linkage assembly is also disposed within the base and opens the arterial conduit when the venous access tube is present in the venous passage and closes the arterial conduit when the venous access tube is removed from the venous passage. Preferably, the first linkage assembly will also open the venous conduit when the venous access tube is present in the venous passage and close the venous conduit when the venous access tube is removed from the venous passage. Optionally, a second linkage assembly may be provided which opens the arterial conduit when the arterial access tube is present in the arterial passage and which closes the arterial conduit when the arterial access tube is removed from the arterial passage. Usually, the second valve assembly will also open the venous conduit when the arterial access tube is present in the arterial passage and close the venous conduit when the arterial access tube is removed from the venous passage.

Typically, the venous and arterial conduits comprise flexible, usually elastomeric, tubes and the linkage assemblies comprise clamps or "pinch valve" mechanisms which are spring-loaded to close the tube in the absence of an access tube in the associated access port. The flexible conduits may be adapted for direct connection to a blood vessel, may have a luer fitting or other standard connection at their distal ends, or may terminate in a fitting on the base of the valve assembly.

The present invention further provides for improved dual port valve assemblies of the type comprising a base, a first access port for receiving an access tube, a second access port for receiving an access tube, a first outlet fluidly connected to the first access port, and a second outlet fluidly coupled to the second access port, wherein the improvement comprises an interlock mechanism which prevents flow between the first access port and the first outlet when there is no access tube present in the second access port.

The present invention still further provides methods for establishing extracorporeal blood circulation for a patient's vasculature. Such methods comprise inserting a first access tube, such as a needle, into a first subcutaneous port to withdraw blood from a blood vessel and transfer such blood into extracorporeal circulation, such as hemodialysis, hemofiltration, hemodiafiltration, apheresis, or the like. A second access tube is inserted into a second subcutaneous port to return blood from such extracorporeal circulation. The method particularly comprises terminating the withdrawal blood from the first subcutaneous port in the event that the second (return) access tube is disconnected from the second access port. Usually, the first subcutaneous access port is attached to an artery and the second subcutaneous access port is connected to a vein, but other combinations are possible as described above. The terminating step preferably comprises actuating a linkage between the first access port and the second access port, wherein the linkage usually closes a conduit which connects the blood vessel to the first subcutaneous port. Typically, insertion of the first access tube into the first subcutaneous port will also cause opening of the second access tube, usually against a spring or other stored-energy mechanism, so that subsequent removal of the access tube will result in immediate reclosing of the second access port in a "fail safe" manner. In preferred aspects of the method, the linkage also closes conduit which connects the blood vessel to the second subcutaneous port, and the method further comprises actuating a second linkage which closes both the first and second access ports in the event that the first access tube is disconnected from the first access port.

When blood withdrawal from the first subcutaneous port terminates as a result of disconnection of the second (return) access tube from the second access port, the extracorporeal circulation system, e.g. dialysis machine, will preferably be able to monitor and detect the flow termination, typically by detecting a decrease in pressure in the first access tube which is connected to the first access port. The pressure decrease, of course, will typically result from closure of the first access port in the manner described above.

DESCRIPTION OF THE SPECIFIC EMBODIMENTS

The present invention provides methods and apparatus for establishing percutaneous access to a patient's blood vessels, including both arterial blood vessels and venous blood vessels, for the purpose of establishing extracorporeal circulation for a variety of therapeutic procedures, as described below. Access port assemblies and systems according to the present invention comprise two ports which are implanted subcutaneously so that a "passage" therein lies a short distance beneath the surface of the patient's skin, typically being within 3 mm to 20 mm of the skin's surface. An access tube may then be percutaneously inserted into the passage in each of the access ports in order to provide connections to the blood vessels via the access ports. Extracorporeal circulation can thus be established for any blood treatment which requires continuous or even intermittent blood circulation, such as hemodialysis, any hemofiltration, hemodiafiltration, apheresis, and the like. In addition to extracorporeal treatment, the dual access port assemblies of the present invention can be used for perfusing drugs, fluids, and other materials directly into a patient's circulation for a variety of purposes.

The present invention relies on implantation of the dual access port assemblies and connection of the assemblies to the target blood vessel(s) via conduit(s), at least a portion of which will usually be flexible. By "flexible," it is meant that the conduit will be resilient and collapsible so that it may be externally clamped, pinched, or otherwise deformed in order to prevent blood flow through the conduit when the access port is to be closed. The use of external clamping to close the conduit is particularly advantageous since no internal structure need be provided within the conduit which could interfere with blood flow and/or with insertion of a needle or other access tube into the conduit.

The access tube will usually be a needle which can be directly pierced (percutaneously introduced) through the patient's skin and into the implanted port. Thus, the needle will usually have a sharpened tip in order to permit it to be self-introduced through the skin. Of course, access tubes having blunt distal ends could be used by first piercing the skin with a separate blade, stylet, needle, or the like, and thereafter introducing the access tube into the resulting incision or hole. The access tube could also be introduced using an internal stylet which is subsequently withdrawn, leaving the tube in place in the port. Generally, the needle or other access tube will possess sufficient column strength in order to actuate a linkage for relieving clamping of the conduit, usually being a rigid metallic or plastic needle or cannula, as described in more detail below.

Figure 1:
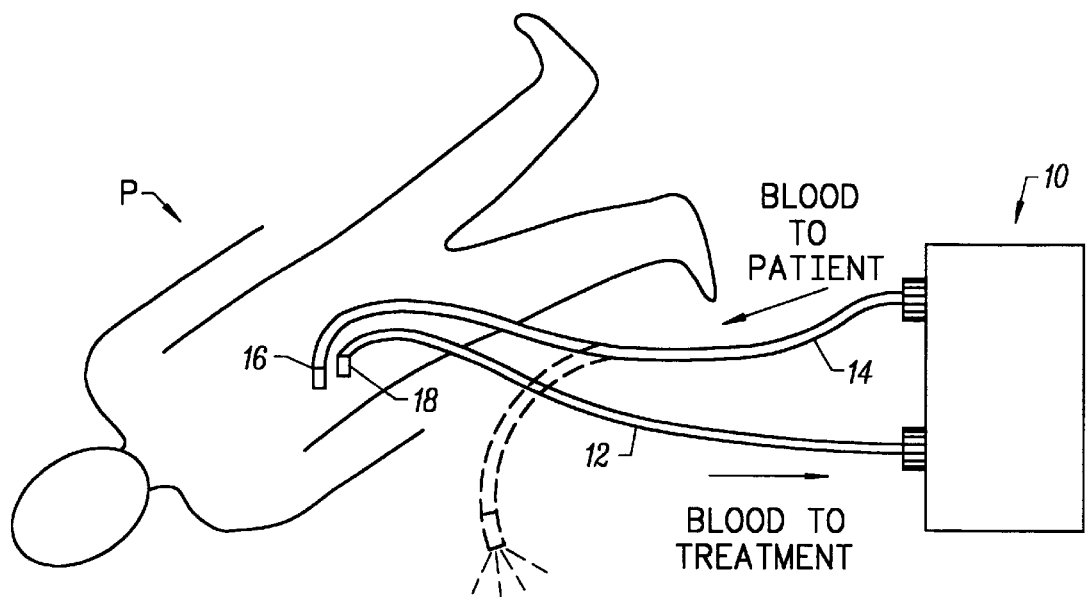
FIG. 1 is a schematic illustration of an extracorporeal blood circulation system employing the dual port valve assembly of the present invention.

Referring now to FIG. 1, an extracorporeal blood treatment apparatus 10, such as a hemodialysis machine, is connected to a patient P using a blood withdrawal line 12 and a blood return line 14. An access tube 16 at the distal end of the blood withdrawal line 12 is percutaneously introduced in a subcutaneous port which has been previously implanted in the patient. Similarly, an access tube 18 at the distal end of the blood return line 14 is percutaneously introduced into a separate subcutaneous access port which has previously implanted into the patient. The details and preferred constructions of the subcutaneous access ports will be described in more detail below.

The present invention is particularly concerned with the situation where the blood return line 14 becomes accidentally dislodged or removed from the associated subcutaneous port, as shown in broken line in FIG. 1. In such circumstances, the extracorporeal treatment apparatus 10 will usually be unable to detect that blood flowing through the return line 14 is being spilled into the environment and not being returned to the patient. Thus, unless the dislodgement of the blood return line 14 is noticed by the patient or operator, and the system turned off, the patient is at risk of excessive blood loss since blood will continue to be drawn from the patient through blood withdrawal line 12 by the apparatus 10. The present invention is particularly intended to prevent such accidental blood loss by terminating blood flow from the access port connected to the blood withdrawal line 12.

The present invention relies on providing an interlock between the withdrawal and return access ports so that blood flow through the withdrawal access port is stopped as a direct consequence of removal of the access tube 16 from the blood return access port. The interlock is preferably mechanical, as described in detail below, but could also be hydraulic, electrical, or the like. Moreover, the various components of the access ports will typically be combined in a single enclosure, referred to herein after as a "base." The assemblies and systems of the present invention, however, could also comprise separate components which could be independently implanted in the patient and interconnected in various ways to provide the desired interlock.

Figure 2:
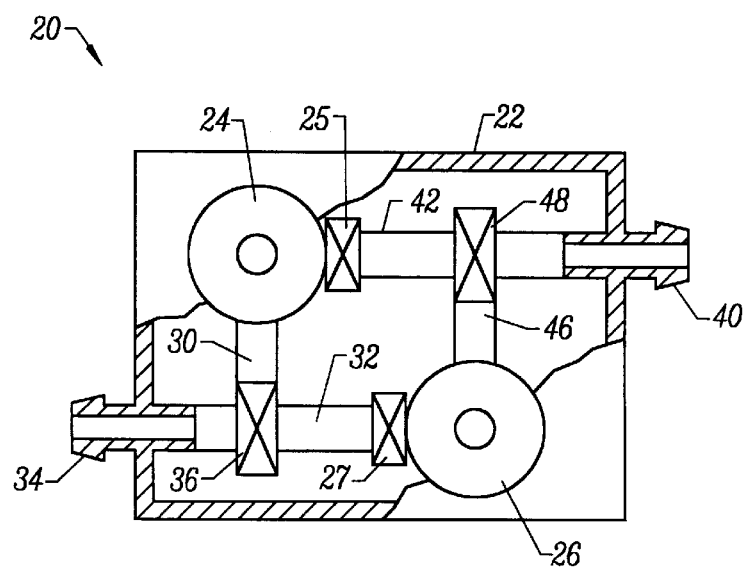
FIG. 2 is a schematic plan view of a dual port valve assembly according to the present invention.

An exemplary dual port valve assembly 20 constructed in accordance with the principles of the present invention is schematically illustrated in FIG. 2. The dual port valve assembly 20 comprises a base 22 having a first access port 24 and second access port 26 therein. Each of the access ports 24 and 26 will be configured to receive an access tube which may take the form of a needle or any of the other structures described above. Preferably, the access ports 24 and 26 will comprise mechanical valve assemblies 25 and 27, respectively, which open and close in response to insertion of the access tube, generally as described in copending provisional application Ser. No. 60/036,124, filed Jan. 21, 1997, the full disclosure of which has previously been incorporated herein by reference. The access port assemblies of the present invention, however, are not limited to mechanical valves, and could also comprise ports 24 and 26 which are formed from penetrable membranes or other conventional needle-access structures.

The present invention requires at least that the absence and/or removal of an access tube from the first access port 24 result in closure of the second access port 26. In dual port valve assembly 20, this is accomplished by a first linkage 30 between the first access port 24 and a conduit 32 which extends from the second access port 26 to an outlet connector 34 on the exterior of the base 22. Usually, the first linkage 30 will be a mechanical linkage which opens a "normally closed" clamp 36 which will close the conduit 32 when the access tube is removed to prevent blood flow from port 26. Thus, the connector 34 may be connected to a blood vessel, typically an artery, to act as a blood supply through port 26. In that case, a second connector 40 which is connected to the first port 24 through conduit 42 will act to return blood to the patient from the extracorporeal treatment system 10.

While the present invention is particularly directed at stopping the withdrawal blood from the patient in the event that the return access tube has been dislodged, the methods and systems will usually provide for stopping flow to and from both access ports in the event that either of the access tubes is lost from either of the access ports. As illustrated in FIG. 2, a second linkage assembly 46 is provided between the second port 26 and the second conduit tube 42. Linkage 46 has a clamp 48 or other closure mechanism which is opened by the presence of an access tube at port 26 and closed by the absence of an access tube in port 26. Port 26 will preferably further include an internal valve mechanism for closing itself when the access tube is lost, as described in copending provisional application Ser. No. 60/036,124. Thus, the dual port valve assembly 20 will provide for closing both access ports 24 and 26 in the event either access tube is lost.

Figure 3:
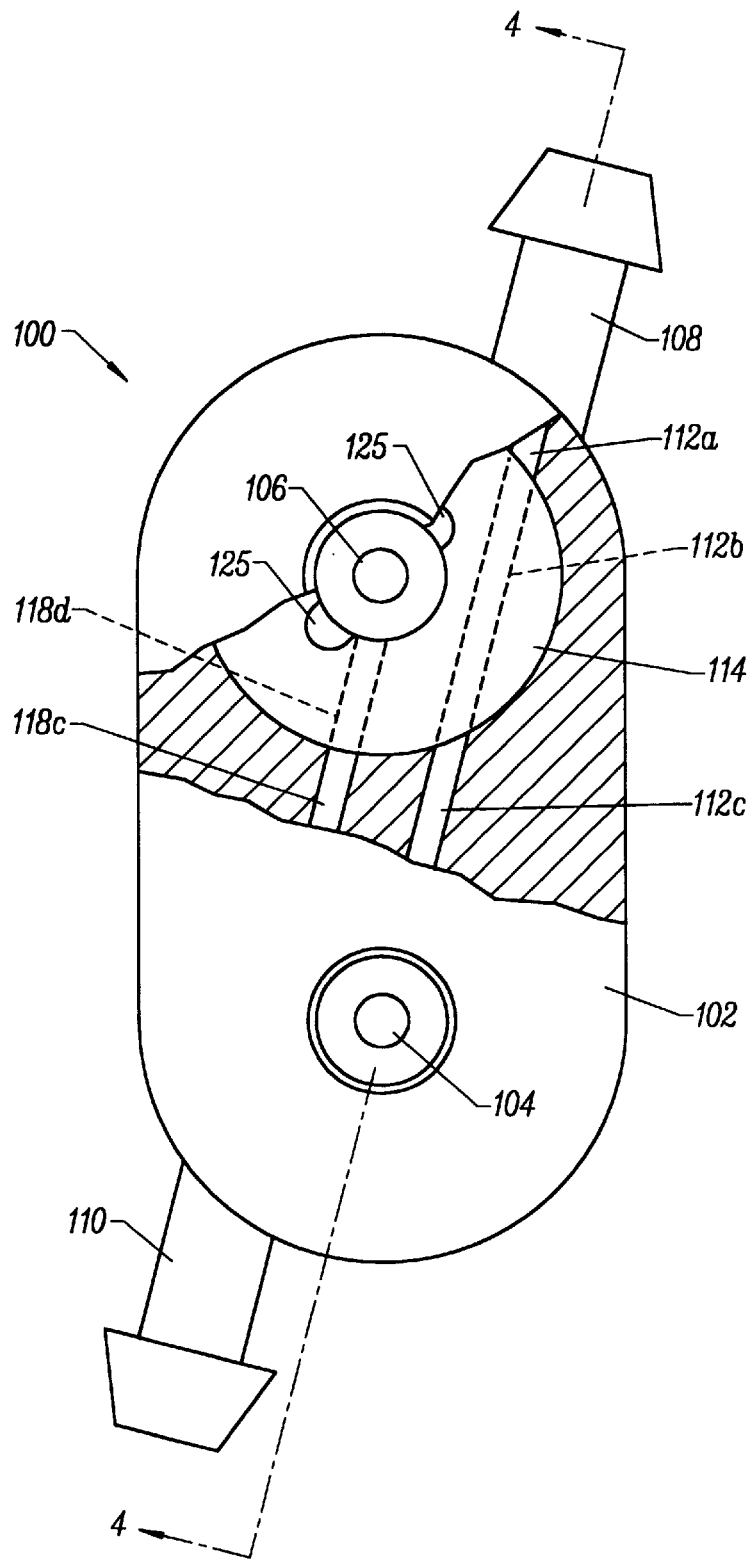
FIG. 3 is a plan view of a dual port valve assembly with portions broken away to show the internal valve passages.
Figure 4:
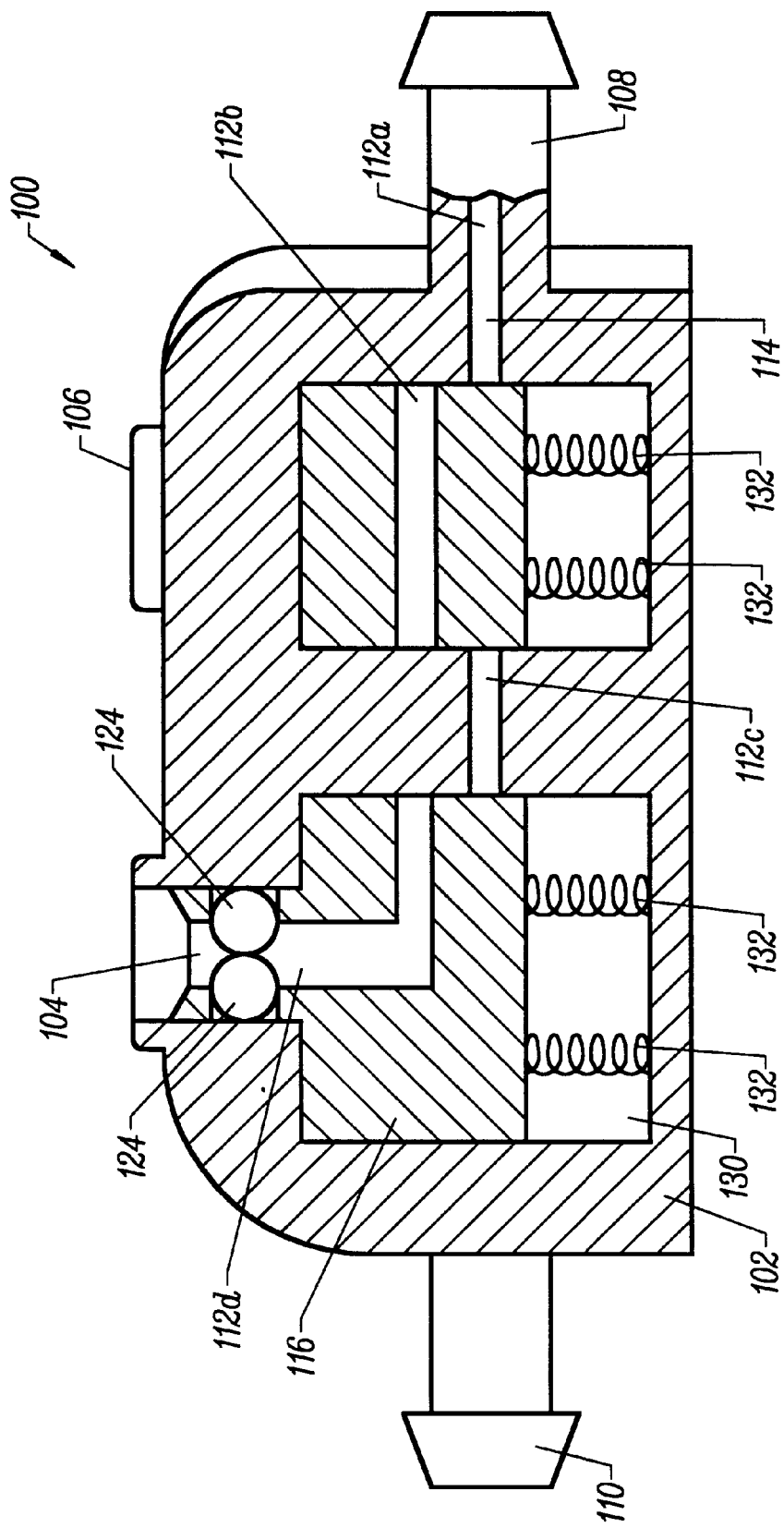
FIG. 4 is cross-sectional view of the valve of FIG. 3 taken along line 4—4 of FIG. 3.
Figure 5:
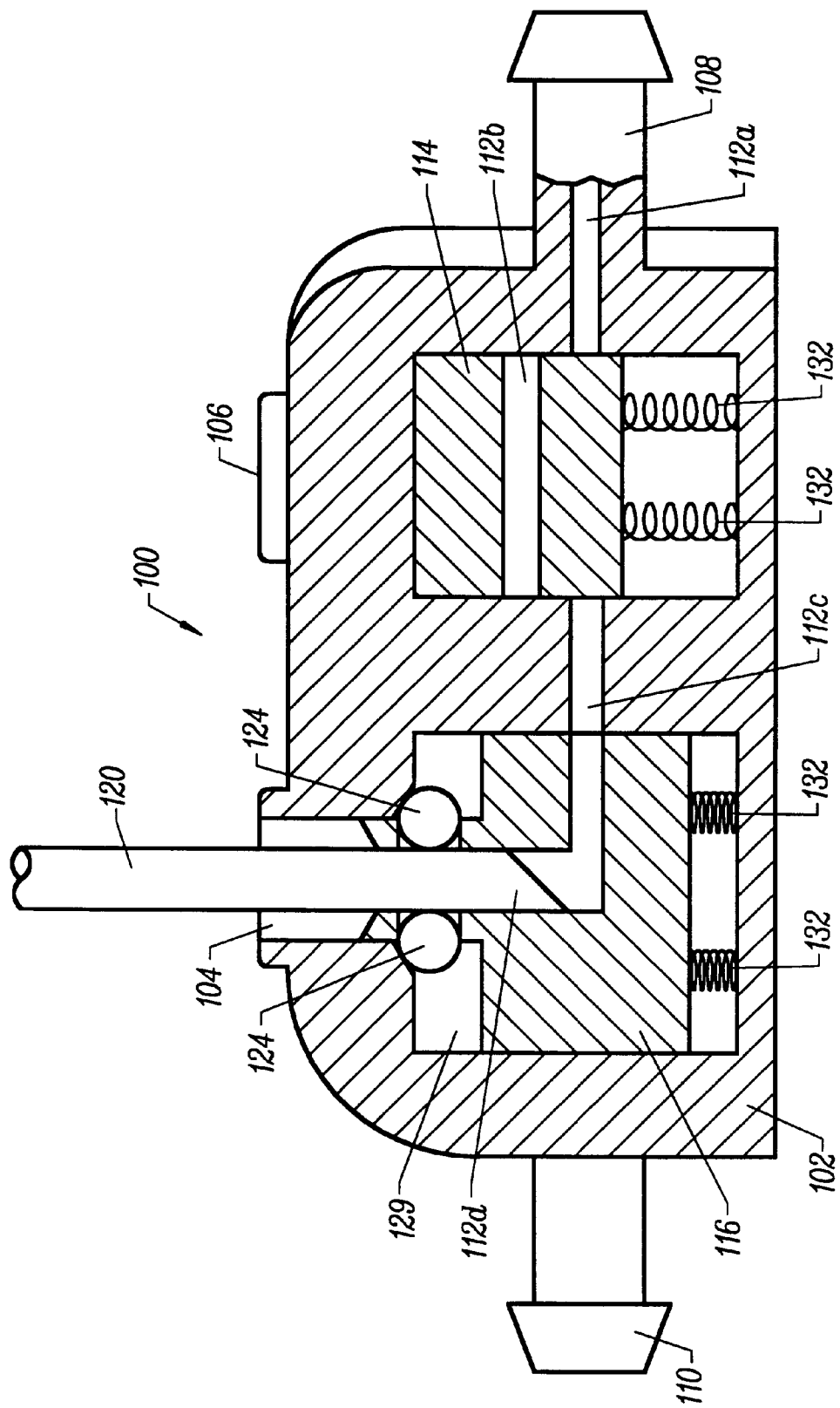
FIG. 5 is a cross-sectional view similar to FIG. 4, except that an access needle is present in a first port.
Figure 6:
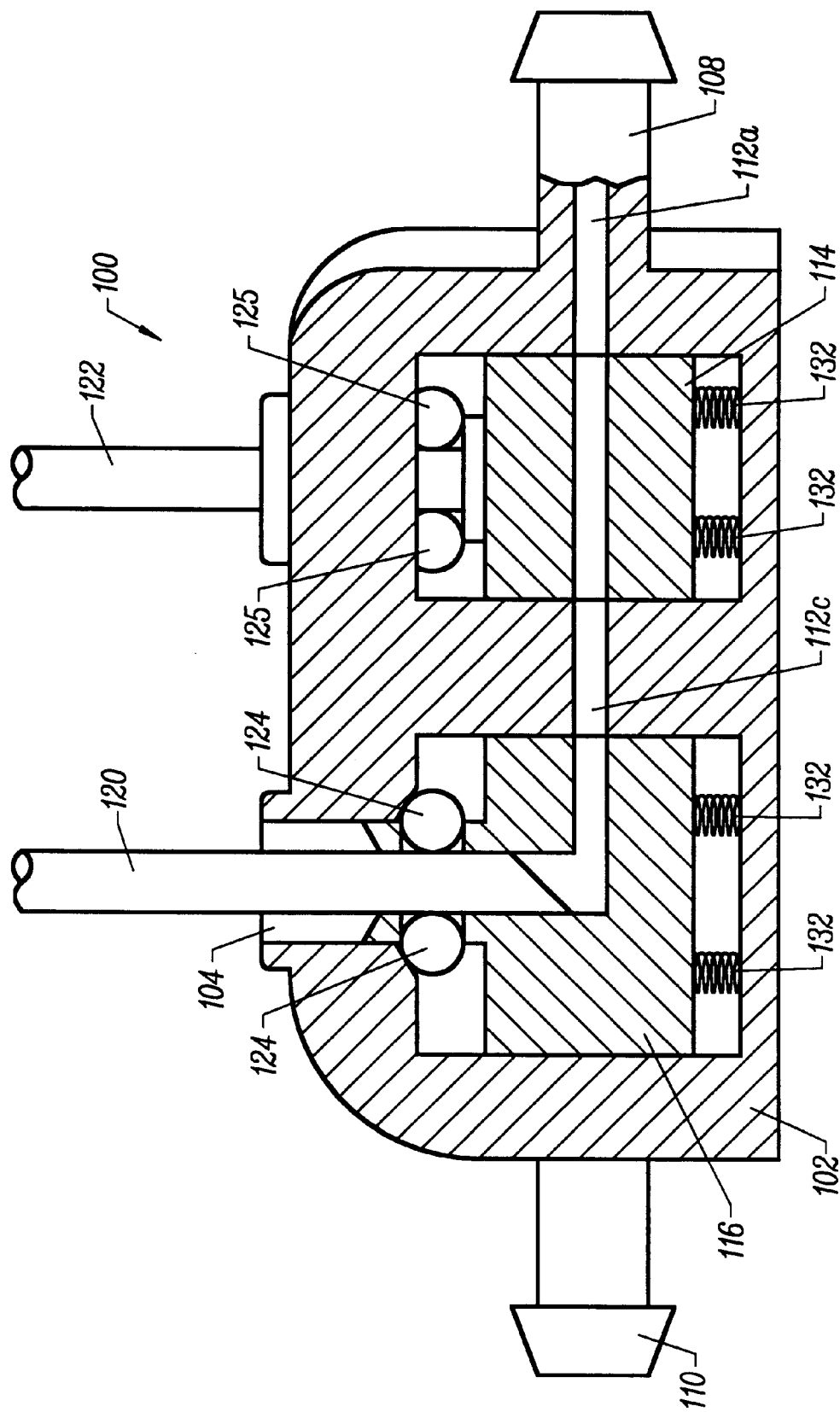
FIG. 6 is a cross-sectional view similar to FIGS. 4 and 5, except that access needles are present in both the first and second ports.

Referring now to FIGS. 3–6, (FIGS. 4–6 are cross-sectional views taken along line 4—4 in FIG. 3) a specific embodiment of the dual port valve assembly 100 comprises a base enclosure 102 and having a first access port 104 and a second access port 106. The base enclosure 102 has a first connector 108 adapted to be removably secured to an implantable cannula which may in turn be attached to an artery or vein in the manner described in the previously incorporated provisional application Ser. No. 60/036,124. A second connector 110 is also provided for connection to an artery or vein in the same manner. The first connector 108 on the base enclosure is fluidly coupled to the first port 104 by a segmented lumen 112 having four segments 112a–112d within the base enclosure 102. The first segment 112a is coaxially aligned within the first connector 108 and extends inwardly to a vertically reciprocatable valve piston 114. The valve piston 114 includes the second lumen segment 112b therein, where the segments 112a and 112b are out of alignment when the valve piston 114 is raised, as shown in FIG. 5. When the valve piston 114 is lowered, however, as shown in FIG. 6, the segments 112a and 112b will be aligned to permit blood flow therethrough.

The third lumen segment 112c is disposed in the middle of the base enclosure 102 and is aligned with the first segment 112a. In this way, when the valve piston 114 is raised, continuity between lumen segment 112a and lumen segment 112c is broken. When the valve piston 114 is lowered, however, continuity between segments 112a and 112c is established to permit blood flow therethrough.

The fourth lumen segment 112d is disposed in a second vertically reciprocatable valve piston 116 which is aligned with the first port 104, as best seen in FIG. 4. Lumen segment 112d is L-shaped and is aligned with the third lumen segment 112c when valve piston 116 is in its lowered position, as shown in FIGS. 5 and 6. When the valve piston 116 is raised, as shown in FIG. 4, the fourth lumen segment 112d is out of alignment with the third lumen segment 112c so that flow is blocked between the first port 104 and the first connector 108. As described thus far, it can be seen that, in order to establish flow from the first port 104 to the first connector 108 (or vice versa), both the valve pistons 114 and 116 must be in their lowered position. It should be noted that a similar four-segment lumen 118 is provided between the second connector 110 and the second port 106. Only two of the segments (third segment 118c and fourth segment 118d) are illustrated in FIG. 3. It will be further understood, however, that in order for the lumen 118 to be fully opened, both the valve pistons 114 and 116 must be in their lowered configuration, as illustrated in FIG. 6.

As will now be described, the valve pistons 114 and 116 are lowered by introducing access needles 120 and 122 into the first and second ports 104 and 106, respectively. As illustrated in FIG. 5, the first access needle 120 is passed into port 104 (which will require percutaneous passage since the port will be implanted) and engages a pair of adjacent balls 124. When the balls 124 are in their radially closed configuration, as seen in FIG. 4, they lie across the port 104. Thus, the needle 120 will engage the balls 124 and move them downward as the needle is depressed. As the balls 124 enter an enlarged portion 129 of chamber 130 within the base enclosure 102, they spread apart allowing the needle to enter the vertical segment of lumen segment 112d, as illustrated in FIG. 5. When the access needle 120 is removed, the valve piston 116 will return to its vertically raised position under the return force of springs 132 which are compressed as the valve piston is initially lowered.

Valve piston 114 is similarly lowered by introducing an access needle 122 through port 106 (FIG. 6). The access needle 122 enters the vertical leg of fourth lumen segment 118b, spreads balls 125, and lowers the valve piston 114 in the manner analogous to that just described for valve piston 116. Thus, when both access needles 120 and 122 are fully introduced into the dual access port 100, the valve pistons 114 and 116 are both lowered, and both of the segmented lumens 112 and 118 are aligned and fully opened. Of critical importance to the present invention, when either needle 120 or 122 is removed, either intentionally or accidentally, the corresponding valve piston will raise under the force of the associated springs 132, thus closing one segment in each of segmented lumens 112 and 118, and completely blocking flow through both lumens of the dual port valve.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A dual port valve assembly comprising:
   a first access port connectable to a conduit or a blood vessel, said first access port having a passage which removably receives an access tube;
   a second access port connectable to a conduit or a blood vessel, said second access port having a passage which removably receives an access tube with a valve which opens and closes the passage; and
   a linkage coupled between the first access port and the second port, wherein the linkage closes the valve in the second access port in absence of an access tube in the first access port.

2. A dual port valve assembly as in claim 1, wherein the passage in the first access port has a valve which opens and closes the passage and wherein the linkage also closes the valve in the first access port in the absence of a tube in the first access port.

3. A dual port valve assembly as in claim 2, further comprising a second linkage coupled between the second access port and the first access port, which the second linkage closes the valve in the first access port and the valve in the second port in the absence of an access tube in the second access port.

4. A dual port valve assembly comprising:
   a base having a venous passage for receiving a venous access tube and an arterial passage for receiving an arterial access tube;
   a venous conduit disposed to establish blood flow with the venous access tube inserted through the venous port;
   a venous valve disposed to permit flow from the venous access tube through the venous conduit when opened and to block flow from the venous access tube through the venous conduit when closed;
   an arterial conduit disposed to establish blood flow with the arterial access tube inserted through the arterial port;
   an arterial valve disposed to permit flow from the arterial access tube through the arterial conduit when opened and to block flow from the arterial access tube through the arterial conduit when closed; and
   a first linkage assembly which opens the arterial valve when the venous access tube is present in the venous passage and which closes the arterial valve when the venous access tube is removed from the venous passage.

5. A dual port valve assembly as in claim 4, wherein the first linkage assembly also opens the venous valve when the venous access tube is present in the venous passage and closes the venous valve when the venous access tube is removed from the venous passage.

6. A dual port valve as in claim 5, wherein the venous and arterial conduits each have a proximal end disposed within the base and a distal end disposed outside of the base.

7. A dual port valve as in claim 6, wherein the distal ends of the conduits are adapted for direct connection to a blood vessel.

8. A dual port valve as in claim 6, wherein the distal ends of the conduits are adapted for connection to one end of a catheter.

9. A dual port valve as in claim 6, wherein the distal ends of the conduits terminate in a luer connector.

10. A dual port valve as in claim 6, wherein the venous and arterial conduits each have a proximal end disposed within the base and a distal end which terminates at a connector on an external surface of the base.

11. A dual port valve as in claim 5, wherein the first linkage assembly is disposed wholly within the base.

12. A dual port valve as in claim 5, wherein the arterial valve is an external clamp on the arterial conduit and the venous valve is an external clamp on the venous conduit, wherein linkage is actuated by passage of the venous access tube into the venous passage which results in release of the clamp from the exterior of the arterial and venous conduits.

13. A dual port valve as in claim 5, wherein the venous passage comprises a tapered bore which seals against the venous access tube as said tube is inserted therein.

14. A dual port valve as in claim 13, wherein the venous conduit is attached to a small diameter and of the tapered bore.

15. A dual port valve as in claim 14, wherein the venous conduit is attached to the tapered bore at an angle from 75° to 105°.

16. A dual port valve assembly as in claim 5, further comprising a second linkage assembly which opens the arterial valve when the arterial access tube is present in the arterial passage and which closes the arterial valve when the arterial access tube is removed from the arterial passage.

17. A dual port valve assembly as in claim 16, wherein the second linkage assembly also opens the venous valve when the arterial access tube is present in the arterial passage and closes the venous valve when the arterial access tube is removed from the venous passage.

18. A dual port valve assembly as in claim 17, wherein the venous and arterial conduits each have a proximal end disposed within the base and a distal end disposed outside the base.

19. A dual port valve assembly as in claim 18, wherein the distal ends of the conduits are adapted for direct connection to a blood vessel.

20. A dual port valve assembly as in claim 18, wherein the distal ends of the conduits are adapted for connection to one end of a catheter.

21. A dual port valve assembly as in claim 18, wherein the distal ends of the conduits terminate in a luer connector.

22. A dual port valve assembly as in claim 17, wherein the venous and arterial conduits each have a proximal end disposed within the base and a distal end which terminates at a connector on an external surface of the base.

23. A dual port valve assembly as in claim 17, wherein the second linkage assembly is disposed wholly within the base.

24. A dual port valve assembly as in claim 17, wherein second arterial valve is an external clamp on the arterial conduit and the venous valve is an external clamp on the venous conduit, wherein linkage is actuated by passage of the arterial access tube into the arterial passage which results in release of the clamp from the exterior of the arterial and venous conduits.

25. A dual port valve assembly as in claim 17, wherein the arterial passage comprises a tapered bore which seals against the arterial access tube as said tube is inserted therein.

26. A dual port valve assembly as in claim 25, wherein the arterial conduit is attached to a small diameter and of the tapered bore.

27. A dual port valve assembly as in claim 26, wherein the arterial conduit is attached to the tapered bore at an angle from 75° to 105°.

28. An improved dual port valve assembly of the type comprising a base, a first access port for receiving an access tube, a second access port for receiving an access tube, a first outlet fluidly connected to the first access port, and a second outlet fluidly coupled to the second access port, wherein the improvement comprises an interlock mechanism which prevents flow between the first access port and the first outlet which there is no access tube present in the second access port.

* * * * *